United States Patent
Hayashi et al.

(10) Patent No.: US 6,500,967 B2
(45) Date of Patent: Dec. 31, 2002

(54) CATALYST FOR USE IN PRODUCTION OF EPOXIDE, METHOD FOR PRODUCING THE CATALYST, AND METHOD FOR PRODUCING EPOXIDE

(75) Inventors: Toshio Hayashi, Kobe (JP); Masahiro Wada, Nishinomiya (JP); Takahiro Inagaki, Hirakata (JP)

(73) Assignee: Nippon Shokubai Co., Ltd., Osaka (JP)

( * ) Notice: Subject to any disclaimer, the term of this patent is extended or adjusted under 35 U.S.C. 154(b) by 30 days.

(21) Appl. No.: 09/788,573

(22) Filed: Feb. 21, 2001

(65) Prior Publication Data

US 2001/0020105 A1 Sep. 6, 2001

(30) Foreign Application Priority Data

Feb. 23, 2000 (JP) .......................................... 2000-052194

(51) Int. Cl.⁷ ............................................ C07D 301/10
(52) U.S. Cl. ........................................ 549/523; 549/533
(58) Field of Search ................................... 549/523, 533

(56) References Cited

U.S. PATENT DOCUMENTS

| | | | |
|---|---|---|---|
| 5,623,090 A | 4/1997 | Haruta et al. | 568/360 |
| 5,932,750 A | 8/1999 | Hayashi et al. | 549/523 |
| 5,939,569 A | 8/1999 | Jones et al. | 549/512 |
| 5,965,754 A | 10/1999 | Clark et al. | 549/533 |
| 6,031,116 A | 2/2000 | Bowman et al. | 549/523 |
| 6,124,505 A | 9/2000 | Haruta et al. | 568/360 |

FOREIGN PATENT DOCUMENTS

JP 10-66870 3/1998

*Primary Examiner*—Ba K. Trinh
(74) *Attorney, Agent, or Firm*—Nixon & Vanderhye, P.C.; Frank P. Presta

(57) ABSTRACT

To provide an epoxide-production-use catalyst that is suitably used for producing an epoxide by partial oxidation of an unsaturated hydrocarbon, a catalyst in accordance with the present invention is obtained by fixing gold fine particles to a carrier containing an oxide containing at least one of titanium and zirconium, and has an acid quantity of not more than 0.1 mmol/g determined by the $NH_3$-TPD method. Such a catalyst for epoxide producing use can be produced by, for instance, fixing gold fine particles to a carrier having an acid quantity of not more than 0.15 mmol/g. The catalyst for epoxide producing use arranged as above is preferably used as a catalyst in partial oxidation of an unsaturated hydrocarbon to produce a corresponding epoxide.

2 Claims, No Drawings

CATALYST FOR USE IN PRODUCTION OF EPOXIDE, METHOD FOR PRODUCING THE CATALYST, AND METHOD FOR PRODUCING EPOXIDE

FIELD OF THE INVENTION

The present invention relates to a catalyst that is suitably used for producing an epoxide by partial oxidation of an olefin compound with use of molecular oxygen in the presence of a reducing substance such as molecular hydrogen, a method for producing the foregoing catalyst for use in production of an epoxide (hereinafter referred to as epoxide-production-use catalyst), and a method for producing an epoxide by using the epoxide-production-use catalyst.

BACKGROUND OF THE INVENTION

An epoxide producing method in which an olefin compound is partially oxidized with molecular oxygen in the presence of a reducing substance such as molecular hydrogen with use of a catalyst made of a titanium-containing oxide with gold fine particles fixed thereto, so as to produce an epoxide corresponding to the foregoing olefin compound, has been conventionally known (the Japanese Publications for Laid-Open Patent Applications No. 127550/1996 [Publication Date: May 21, 1996], 5590/1998 [Publication Date: Jan. 13, 1998], 244156/1998 [Publication Date: Sep. 14, 1998], and 128743/1999 [Publication Date: May 18, 1999] (Tokukaihei 8-127550, 10-5590, 10-244156, and 11-128743), and U.S. Pat. No. 5,939,569, etc.).

The foregoing catalyst exhibits a certain degree of activity at an initial stage of epoxidation, but the activity lowers as the reaction time has passed. Therefore, the catalyst presents a problem that its activity becomes insufficient when the reaction becomes in a steady state. Further, it also presents a problem that regeneration of the activity is hardly achieved even if a high-temperature heat treatment in an oxygen-containing gas for reactivation of the catalyst is applied to the catalyst whose activity has lowered.

SUMMARY OF THE INVENTION

The present invention was made in light of the foregoing problem in prior art, and an object of the present invention is to provide an epoxide-production-use catalyst that is, for instance, suitably used in partial oxidation of an unsaturated hydrocarbon to produce an epoxide corresponding to the unsaturated hydrocarbon, a method for producing the catalyst, and a method for producing an epoxide with use of the catalyst for epoxide production.

The inventors of the present invention studied the foregoing conventional catalysts, with view to solving the aforementioned problems. Consequently, they discovered that a cause of deactivation of the catalyst formed by fixing gold fine particles to a carrier containing an oxide containing at least one of titanium and zirconium is mainly related to the properties of acidic sites of the catalyst per se.

More specifically, an epoxide produced in epoxidation of an olefin is easily isomerized according to the acidic sites of the epoxide-production-use catalyst, thereby becoming an aldehyde corresponding thereto. For instance, in the case where propylene oxide is produced, propionaldehyde is produced by the foregoing isomerization. Further, in the case where the propionaldehyde resulting from the isomerization was solely brought into contact with the foregoing epoxide-production-use catalyst, an increase in the weight of the epoxide-production-use catalyst per se was observed. Further, in the case where epoxidation of propylene was carried out with use of the epoxide-production-use catalyst having been brought into contact with propionaldehyde, explicit deactivation was observed. Thus, it was found that aldehydes produced by isomerization condensed or polymerized at the acidic sites thereby becoming condensates or polymers that cover the active sites and impair the activity of the epoxide-production-use catalyst.

The inventors of the present application further made earnest study about the foregoing epoxide-production-use catalyst. As a result, among indices indicative of the properties of acidic sites, "acid quantity (for detailed explanation, see the head of the "DESCRIPTION OF THE EMBODIMENTS" section)" that is derived from a quantity of, among ammonium that has been adsorbed on the foregoing epoxide-production-use catalyst, a portion desorbed from the same is particularly significant for maintenance of catalyst activity and also regeneration of the activity.

More specifically, the epoxide-production-use catalyst in accordance with the present invention is composed of (i) a carrier containing an oxide containing at least one of titanium and zirconium, and (ii) gold fine particles fixed onto the carrier, and is arranged so as to have an acid quantity of not more than 0.1 mmol/g, the acid quantity being derived from a quantity of ammonium that, having been adsorbed on the catalyst at temperature of 50° C., is desorbed from the catalyst as the temperature rises from 50° C. to 400° C.

The epoxide-production-use catalyst arranged as above enables production of an epoxide with a high yield and a high selectivity, and further, exhibits good catalyst performance, such as less deactivation. In other words, the present invention ensures that an epoxide-production-use catalyst is provided that is suitably used for partial oxidation of an unsaturated hydrocarbon with molecular oxygen in the presence of a reducing substance so as to produce an epoxide, that is superior in activity and selectivity, and that exhibits less deactivation and easy regeneration of activity.

Furthermore, a method for producing the epoxide-production-use catalyst in accordance with the present invention is a method including the step of fixing gold fine particles to a carrier, the carrier containing an oxide that contains at least one of titanium and zirconium and having an acid quantity of not more than 0.15 mmol/g, the acid quantity being derived from a quantity of ammonium that, having been adsorbed on the catalyst at temperature of 50° C., is desorbed from the catalyst as the temperature rises from 50° C. to 400° C. This method makes it possible to produce the catalyst having excellent performance.

Furthermore, a method for producing an epoxide in accordance with the present invention includes the step of partial oxidation of an unsaturated hydrocarbon with molecular oxygen in the presence of a reducing substance, with use of a catalyst, the catalyst being arranged so as to include a carrier containing an oxide containing at least one of titanium and zirconium as well as gold fine particles fixed onto the carrier, and to have an acid quantity of not more than 0.1 mmol/g, the acid quantity being derived from a quantity of ammonium that, having been absorbed in the catalyst at temperature of 50° C., is desorbed from the catalyst as the temperature rises from 50° C. to 400° C. This method makes it possible to produce an epoxide from an unsaturated hydrocarbon with a high yield.

For a fuller understanding of the nature and advantages of the invention, reference should be made to the ensuing detailed description.

DESCRIPTION OF THE PREFERRED EMBODIMENTS

An epoxide-production-use catalyst in accordance with the present invention (hereinafter referred to simply as "catalyst in accordance with the present invention" as required) is a catalyst that is obtained by fixing gold fine particles to a carrier containing an oxide containing at least one of titanium and zirconium, (hereinafter referred to simply as "gold-fine-particles-containing catalyst" as required), and that catalyst has an acid quantity, described below, of not more than 0.1 mmol/g. First of all, the definition of "acid quantity" and a measurement method of the same in the present invention will be described below.

Measurement of the acid quantity was performed employing TPD-70 (trade name, available from BEL JAPAN INC.) as measuring apparatus, in the following manner. First of all, about 0.5 g (W g) of a sample of acid quantity measurement (hereinafter referred to as measurement object) was accurately weighed and brought into the foregoing measuring apparatus. Subsequently, the sample was held at 280° C. for 30 minutes while helium gas was flown through the measuring apparatus at flow rate of 50ml/minute, so that water adsorbed on the measurement sample was removed. Thereafter, the temperature was lowered to 50° C., and ammonium gas was caused to adsorb on the measurement sample under conditions of 50° C. and 200 mmHg (about 0.263 atm) for 10 minutes. Then, after the inside of the measuring apparatus was vacuumed to $10^{-3}$ mmHg (about $1.31 \times 10^{-6}$ atm), the temperature inside the measuring apparatus was raised from 50° C. to 400° C. at a rate of 10° C. per minute while helium gas was flown therethrough at flow rate of 50 ml/min, and a quantity of ammonium that is desorbed from the measurement object was determined by a mass spectrometer. The "acid quantity" in the present invention is defined as a value of the number of moles (mmol) of desorbed ammonium divided by the weight (W g) of the measurement object. Incidentally, the aforementioned method for measuring a quantity of desorbed ammonium is sometimes referred to as "$NH_3$-TPD method".

In the case where the acid quantity of the foregoing gold-fine-particles-containing catalyst is not higher than 0.1 mmol/g (i.e., the catalyst is in accordance with the present invention), which means that catalyst activity is high in the partial oxidation of an unsaturated hydrocarbon, it is possible to produce an epoxide with a high yield and a high selectivity. Besides, good catalyst activity can be maintained for a longer time than conventionally. Furthermore, catalyst activity, once lowered, can be easily regenerated by, for instance, a heat treatment with use of an oxygen-containing gas.

On the other hand, in the case where the acid quantity of the foregoing gold-fine-particles-containing catalyst exceeds 0.1 mmol/g, deactivation of the catalyst is remarkably promoted with time. Furthermore, if the gold-fine-particles-containing catalyst, after employed for an epoxidation reaction for several hundreds of hours, is subjected to a heat treatment by raising the temperature from 100° C. to 500° C. in the presence of an oxygen-containing gas as an attempt to regenerate the catalyst activity, resultant regeneration of activity is remarkably insufficient.

Incidentally, the degree of deactivation of the gold-fine-particles-containing catalyst and the degree of regeneration of the activity thereof vary particularly with the acid quantity, among the properties of acidic sites, and further, it also varies with "strength of acidic sites" as well, which is another criterion of the acidic sites. More concretely, a peak temperature of the desorption of ammonium (i.e., the temperature at which an quantity per unit time of ammonium desorbed from the catalyst exhibits a peak, the ammonium having been absorbed by the catalyst at 50° C.) by the foregoing $NH_3$-TPD method is preferably not higher than 150° C. When the peak temperature exceeds 150° C., the strength of acidic sites becomes excessively great, thereby causing epoxide generated to polymerize or condense easily. Moreover, since the desorption of once polymerizing or condensing substance from the gold-fine-particles-containing catalyst is difficult, regeneration of the catalyst whose activity has lowered becomes more difficult as well.

A method for producing the catalyst in accordance with the present invention is not particularly limited, and may be a method in which gold fine particles are fixed to a carrier that contains an oxide containing at least one of titanium and zirconium and that has an acid quantity, described above, of not more than 0.15 mmol/g.

Examples of methods for preparing a carrier whose acid quantity is adjusted to the foregoing range (carrier before acid quantity adjustment is described below in detail) include, for instance, (1) a method for preparing a carrier so that at least one kind of an element should be further carried thereon, the element being selected from among the group consisting of alkaline metal elements, alkaline earth metal elements, rare earth elements, and thallium elements (hereinafter referred to as acid quantity adjustment element carrying method), (2) a method where, before a gold compound is caused to adhere to or bonded with a carrier, at least one kind of an organic compound selected from among the group consisting of alcohols, ketones, ethers, esters, and others is brought into contact with the carrier in the absence of water, in a heated environment as required, and subsequently a heat treatment at a temperature from 150° C. to 450° C. is applied (hereinafter referred to as contact heat-treatment method), (3) a method where a carrier is silylated with use of a silylating reagent (hereinafter referred to as silylating method), (4) a method where a carrier is processed with at least one kind of an electron donor compound (hereinafter referred to as electron donor compound employing method), and (5) a method where a carrier is processed with heat in an atmosphere at a temperature from 500° C. to 1200° C., or more preferably, from 750° C. to 1000° C. (high-temperature calcination method). By any one of the methods, the acid quantity is decreased, ensuring that a carrier with an acid quantity of not more than 0.15 mmol/g is easily prepared.

Examples of alkaline metal elements used in the foregoing acid quantity adjustment carrying method (1) includes lithium, sodium, kalium, rubidium, cesium, and francium. Examples of alkaline earth metal elements include beryllium, magnesium, calcium, strontium, barium, and radium. Examples of rare earth elements include lanthanum, cerium, and samarium. Thallium is an example of another element applicable. Among the aforementioned elements, sodium, kalium, rubidium, cesium, magnesium, calcium, strontium, and barium are more preferable. Incidentally, a content of an individual element or a sum of the same in combination is not particularly limited as long as the acid quantity of the carrier prepared with the same does not exceed 0.15 mmol/g, but it is preferably in a range of 0.001 percent by weight (wt %) to 20 wt %, more preferably in a range of 0.5 wt % to 5 wt %, and further more preferably in a range of 0.01 wt % to 2 wt %.

Incidentally, needless to say, in the case where a carrier that contains an oxide containing at least one of titanium and zirconium is formed with the foregoing oxide fixedly provided (carried) onto a support such as silica, the foregoing element may be fixed to the support before the oxide is carried thereon, or it may be carried thereon simultaneously or after the foregoing oxide is carried thereon.

In the contact heat-treatment method (2), the fashion to bring the carrier in contact with an organic compound is not particularly limited. For instance, (a) a carrier may be immersed in the foregoing organic compound in a liquid phase, (b) a carrier may be washed in the foregoing organic compound in a liquid phase, or (c) a carrier may be exposed to the organic compound in a gas phase. Furthermore, examples of alcohols used in the contact heat-treatment method include methyl alcohol, ethyl alcohol, isopropyl alcohol, n-butyl alcohol, octyl alcohol, and ethylene glycol. Examples of ketones include acetone, methylethylketone, and methylisobutylketone. Examples of ethers include tetrahydrofuran, and diisobutylether. Examples of esters include ethyl acetate, butyl acetate, and methyl propionate.

Incidentally, in the case where the carrier and organic compound are brought into contact in a heated environment, the temperature as a heating condition is preferably higher than room temperature and not higher than 1000° C., or more preferably in a range from 50° C. to 300° C. The other conditions such as a processing time, a quantity and kind of an organic compound, etc. may be set so that the acid quantity of the carrier after the contact and heat treatment should be not more than 0.15 mmol/g.

Examples of silylating reagent used in the foregoing silylating method include organic silanes, organic silylamines, and organic silazanes. The organic silanes include chlorotrimethylsilane, dichlorodimethylsilane, chlorobromodimethylsilane, nitrotrimethylsilane, chlorotriethylsilane, chlorodimethylphenylsilane, dimethylpropylchlorosilane, dimethyloctylchlorosilane, tributhylchlorosilane, dimethoxymethylchlorosilane, methoxytrimethylsilane, dimethoxydimethylsilane, metyltrimethoxysilane, dimethoxydiphenylsilane, trimethoxyphenylsilane, ethoxytrimethylsilane, ethyltrimethoxysilane, diethoxydimethylsilane, diethoxydiethylsilane, ethyltriethoxysilane, trimethylisopropoxysilane, methoxytripropylsilane, butyltrimethoxysilane, octyltrimethoxysilane, and acetoxytrimethylsilane.

Examples of organic silylamines include dimethylaminotrimethylsilane, diethylaminotrimethylsilane, N-trimethylsilyldimethylamine, bis(dimethylamino)dimethylsilane, methylsilatrane, N-trimethylsilylimidazole, and N-trimethylsilylpyrrolidine.

Examples of organic silazanes include hexamethyldisilazane, heptamethyldisilazane, 1,1,3,3-tetramethyldisilazane, and 1,3-diphenyltetramethyldisilazane.

Examples of the other silanizers include tetramethoxysilane, tetraethoxysilane, 3-aminopropyltrimethoxysilane, 3-cyanopropyltrichlorosilane, 2-cyanoethyltrimethoxysilane, mercaptomethyltrimethoxysilane, dimethoxy-3-mercaptopropylmethylsilane, 3-mercaptopropyltrimethoxysilane, 3,3,4,4,5,5,6,6,6-nonafluorohexyltrichlorosilane, trimethylsilyltrifluoromethane sulfonate, N,O-bistrimethylsilylacetoamide, N-trimethylsilylacetoamide, and N,N'-bistrimethylsilyl urea.

Incidentally, a processing time for silylation, a quantity and kind of the silylating reagent used, etc. may be set so that the acid quantity of the resultant carrier should be not more than 0.15 mmol/g.

Examples of the electron donor compounds used in the electron donor compound employing method (4) include nitrogen-containing compounds, sulfur-containing compounds, and phosphorus-containing compounds. Nitrogen-containing compounds, though not particularly limited, include: aliphatic amines such as morpholine and its derivatives, and aromatic amines such as aniline, pyridine, picoline, lutidine, quinoline, pyrrole, indole, carbazole, and derivatives of these compounds. The foregoing nitrogen-containing compounds may be any one of primary amine, secondary amine, and tertiary amine. Sulfur-containing compounds, though not particularly limited, include thiols such as phenylmercaptane, sulfides, disulfides, thiophene, benzothiophene, and derivatives of these compounds. Phosphorus-containing compounds include primary phosphines, secondary phosphines, tertiary phosphines, and phosphine oxides, though not particularly limited.

Incidentally, a processing time for processing an electron donor compound, a quantity and kind of the electron donor compound used, etc. may be set so that the acid quantity of the resultant carrier should be not more than 0.15 mmol/g.

Examples of atmospheres in the heat treatment in the foregoing high-temperature calcination method (5) include a oxygen-gas-containing atmosphere, a hydrogen-gas-containing atmosphere, and an atmosphere containing an inert gas such as argon, helium, or nitrogen. Incidentally, a processing time, etc. for high-temperature calcination may be set so that the acid quantity of the resultant carrier should be not more than 0.15 mmol/g.

These methods (1) through (5) for adjusting the acid quantity of the carrier may be used individually, or more than two selected from the same may be used in combination as required.

The "carrier" used in the present invention that is processed by the foregoing acid quantity adjusting method so as to have an acid quantity of not more than 0.15 mmol/g is not particularly limited, as long as it is characterized by: (1) containing an oxide containing at least one of titanium and zirconium; (2) being capable of carrying gold fine particles; and (3) having an acid quantity exceeding 0.15 mmol/g before being processed.

The kind of the oxide containing at least one of titanium and zirconium (hereinafter referred to simply as oxide as required) is not particularly limited, but examples of oxides containing titanium (titanium-containing oxide) include, for instance, titanium oxides, titanium-containing composite oxides, and titanium-containing silicates. Among these titanium-containing oxides, those having a relatively great specific surface area are particularly preferable. Note that the shape of the titanium-containing oxide is not particularly limited, and it may be used in particulate form.

Among the foregoing titanium-containing oxides, titanium oxides having a primary particle diameter in a range of 10 nm to 200 nm and a relatively great specific surface area of not less than 5 $m^2/g$ are more preferable. Incidentally, however, the primary particle diameter and the specific surface area of titanium oxides are not particularly limited to the above-described ranges.

The foregoing titanium-containing composite oxide is not particularly limited as long as it is a composite formed with titanium that is chemically bonded with another element, such as silicon, via oxygen atoms. More specifically, it is preferably a titanium-containing composite with a relatively large specific surface area, such as titania-silica, titania-alumina, or titania-zirconia. Among these titanium-containing composite oxides, those formed with an oxide carrier that has a specific surface area of not less than 50 $m^2/g$ and that carries a titanium oxide with a high density dispersion are more preferably applicable.

The foregoing titanium-containing silicate is not particularly limited as long as it is a silicate containing titanium. A porous material containing titanium in silica matrix is particularly preferable among others, and it is more preferably applicable if it has a relatively large specific surface area and is arranged so that titanium atoms ($Ti^{4+}$) is isolatedly dispersed in the silicate with a high density. Such titanium-containing silicates are known, examples of which include a material in which some of aluminum atoms composing a zeolite (X,Y type, ZSM-5, ZSM-48, etc.) material are substituted with titanium atoms so that titanium atoms are incorporated in the zeolite lattice; a material in which a part of mesoporous silica (MCM-41, MCM-48, MCM-50, etc.) having mesopores is substituted with titanium atoms; and titanosilicalite (TS-1, TS-2, etc.), which is a composite oxide of titanium and silicon and is microporous. It is also possible to use a material prepared by causing any one of these titanium-containing silicates to carry a very small quantity of titanium oxide with a high dispersion.

An atomic ratio between titanium and silicon (Ti/Si) in a titanium-containing silicate is preferably in a range of 0.1/100 to 20/100, or more preferably in a range of 1/100 to 10/100. A catalyst obtained with use of a titanium-containing silicate in which a ratio of titanium is smaller than that described above has substantially identical catalyst performance to those of a catalyst in which simple silica is used as a carrier. This is incapable of causing selective partial oxidation of olefin that is an unsaturated hydrocarbon, therefore not preferable at all.

On the other hand, examples of oxide containing zirconium (hereinafter referred to as zirconium-containing oxide as required) include zirconium oxides, zirconates, zirconium-containing composite oxides, silicates that contains zirconium and that has a porous structure (referred to as zirconium-containing silicate as required) Among these zirconium-containing oxides, those which have large specific surface areas are particularly preferable. Incidentally, the shape of zirconium-containing oxide is not particularly limited and may be used in particulate form.

Both amorphous and crystalline zirconium oxides are included in the classification of the foregoing zirconium oxides. Taking zirconium dioxide as an example, those in crystal phases such as monoclinic, rhombic, and tetragonal phases are included as crystalline oxides.

The foregoing zirconates also may be amorphous or crystalline. Examples of zirconates include zirconates of alkaline metal, alkaline earth metal, lanthanoid metal, and actinoid metal. More concretely, magnesium zirconate, and sodium zirconate may be taken as examples.

The aforementioned zirconium-containing composite oxide is not particularly limited as long as it is a composite of zirconium chemically bonded with another element, for instance, silicon , via oxygen atoms. Concretely, oxides prepared by high-dispersion of zirconium over amorphous or crystalline silica, oxides prepared by dispersing zirconium over magnesium silicate or barium silicate are taken as examples.

Examples of the aforementioned silicates that contains zirconium and that has a porous structure (zirconium-containing silicates) include amorphous and crystalline zirconosilicates. Zirconium atoms contained in zirconosilicate are often substituted with silicon atoms in silicate. Concretely, zeolite and zirconosilicates having the molecular-sieve structure are taken as examples, and with regard to pores, zirconosilicates having micropores or mesopores are taken as examples. More concretely, the examples include zirconosilicates formed by incorporating zirconium in ZSM-5, ZSM-11, zeolite beta, and MCM-41.

The "carrier" in the present invention may be composed of only a single kind selected from among the aforementioned oxides that contain at least one of titanium and zirconium, or may be composed of a plurality of the same in combination. Further, to improve the activity of epoxide-production-use catalyst finally obtained, for instance, a material obtained by fixing any one of the oxides to a support molded beforehand (described below) may be employed as the carrier.

As the "support", it is possible to use a material composed of a metal oxide or a metal of various kinds that contains neither titanium nor zirconium. Examples of materials of the support include: silica (silicon dioxide), alumina, magnesia, cordierite, zirconium oxide as a metal oxide, and ceramics as composites of these oxides; and foamed substances, honeycomb carriers (support) and pellets made of various metals. Any one of the foregoing supports may be used, or two or more selected from among those may be used in combination as required.

With a view to improving the activity of the catalyst in accordance with the present invention, among the supports mentioned above, those containing at least one of alumina and silica are preferable, or those containing silica are particularly preferable. Incidentally, cases indicated by "containing alumina or silica" include cases in which the support contains zeolite (aluminosilicate) or silica-alumina.

Furthermore, the foregoing crystalline structure, shape, and size of the foregoing support are not particularly limited, but its specific surface area is preferably not less than 50 $m^2/g$, or more preferably not less than 100 $m^2/g$. In the case where the specific surface area is in the foregoing range, side reaction such as successive oxidation of a reaction product is further suppressed. In other words, the reaction for producing only a target reaction product by partial oxidation of a reactant is more selectively and efficiently carried out, whereby the performance of the catalyst in accordance with the present invention is further enhanced.

The ratio of an oxide containing at least one of titanium and zirconium to a support in the case where the oxide is fixed to the support is not particularly limited, but a ratio by weight of the oxide to the support (weight of oxide:weight of support) is preferably in a range of 1:100 to 50:100.

A method for fixing the oxide to the support (causing the oxide to be fixed onto the support) is not particularly limited, but a conventional known method is applicable, such as the sol-gel method employing alcoxide, kneading, or coating in the case where any one containing silica or alumina is used as the foregoing support. Such a method enables high dispersion of the foregoing oxide over the support in an island structure.

With a view to further improving the activity of the catalyst, it is possible to cause the following element to be carried on (contained in) the support as a component element of the catalyst in accordance with the present invention: elements of the groups 5A through 7A including vanadium, molybdenum, and manganese; elements of the group 8 including iron, cobalt, and ruthenium; elements of the groups 1B through 4B including copper, zinc, aluminum, and tin; elements of the groups 5B and 6B including phosphorus and sulfur; and elements of the group 7B including chlorine. For instance, even if an acidic element such as aluminum or molybdenum is contained, it is possible to render the "acid quantity" of the catalyst in accordance with the present invention in the foregoing prescribed range, by applying the aforementioned processing operation for lowering the acid quantity.

By fixing gold fine particles to the foregoing carrier processed so as to have an acid quantity of not more than 0.15 mol/g (more specifically, a titanium-containing oxide and/or a zirconium-containing oxide contained in the carrier), an epoxide-production-use catalyst in accordance with the present invention is produced. The size of the gold fine particle is not particularly limited, but so-called ultra-fine particles having an average particle diameter of not more than 10 nm are preferable. Further, gold carried by the carrier is preferably at a ratio of not less than 0.001 wt % with respect to a total weight of a titanium-containing oxide and a zirconium-containing oxide contained in the carrier, more preferably in a range of 0.001 wt % to 20 wt % or further more preferably in a range of 0.02 wt % to 10 wt %. An amount of carried gold of less than 0.001 wt % is not preferable since it causes the activity of the epoxide-production-use catalyst to lower. On the other hand, an amount of carried gold of more than 20 wt % is not preferable, either, since in such a case a further improvement of the activity of the epoxide-production-use catalyst is hardly expected as compared with the case where gold is carried at a ratio in the foregoing range, and it follows that gold is wastefully used.

To cause gold fine particles to be carried on the foregoing carrier, methods applied when gold fine particles are fixed to the carrier containing an oxide that contains at least one of titanium and zirconium can be adopted without particular limitations. More specifically, the following methods are applicable: (1) a method in which a gold-containing solid substance is obtained by vapor deposition of a gold compound on a carrier, then it is calcined; and (2) a method including a step (Step A) of preparing a solution of a gold compound dissolved in an appropriate solvent, bringing the carrier into the solution, and thereafter removing the solvent from the solution, and a step (Step B) of applying a heat treatment (calcination) a gold-containing solid substance remaining after removal of the solvent, the Steps A and B being performed in the stated order. By so doing, a gold-containing composite having gold fine particles fixed on a carrier, that is, an epoxide-production-use catalyst in accordance with the present invention is produced. Incidentally, applicable as Step A are the co-precipitation method, and the deposition method, as well as common methods such as the impregnation method, the soaking method, the ion exchanging method, etc.

By the impregnation method, a carrier is dipped in a solution dissolving a gold compound homogeneously, left for a certain period of time, and subsequently a solvent is removed by evaporation, whereby a carrier having surfaces that the gold compound in the solution adheres to or is bonded with (gold-containing solid substance) is obtained. The removal of the solvent can be carried out, for example, by means of a device such as an evaporator under reduced or normal pressures, optionally while heated.

By the soaking method, a carrier is soaked in a solution dissolving a gold compound homogeneously, then, the solution is left to stand or stirred for a certain period of time, and subsequently filtered. Consequently a carrier having surfaces that the gold compound in the solution adheres to or is bonded with (gold-containing solid substance) is filtered out. The gold-containing solid substance may be washed with an appropriate solvent as required. The temperature upon either allowing the solution with the carrier therein to stand or stirring the same is determined with thermal stability of the used gold compound taken into consideration, but generally it is preferably in a range of 0° C. to 150° C. Further, the leaving time or the stirring time is not particularly limited, but it is preferably in a range of 1 second to 24 hours.

By the ion exchanging method, a carrier capable of ion exchanging is brought into a solution in which a gold compound is uniformly dissolved and present in an ion form, then the solution is left to stand or stirred for a certain period of time, and subsequently the solution is filtered. Consequently a carrier having a surface bonded with the gold compound in the solution (gold-containing solid substance) is filtered out. The gold-containing solid substance filtered out may be washed with an appropriate solution as required. The temperature upon either allowing the solution with the carrier therein to stand or stirring the same is determined with thermal stability of the used gold compound taken into consideration, but generally it is preferably in a range of 0° C. to 150° C. Further, the leaving time or the stirring time is not particularly limited, but it is preferably in a range of 1 second to 24 hours. Incidentally, water is preferably used as a solvent for dissolving the foregoing gold compound and a solvent for washing the gold-containing solid substance.

Examples of the gold compounds used in the foregoing Step A, though not particularly limited, include: chloroauric acids such as tetrachloroauric (III) acid; sodium chloroaurates such as sodium tetrachloroaurate (III); gold cyanides and kalium cyanoaurates such as gold (I) cyanide and kalium dicyanoaurate (I); diethylamine gold (III) trichloride; gold chloride ethylenediamine$_{13}$ tetraacetate; $(CH_3)_2Au(CH_3COCHCOCH_3)$; $(CH_3)_2Au(CF_3COCHCOCH_3)$; $(CH_3)_2Au(CF_3COCHCOCF_3)$; $(C_2H_5)_2Au(CH_3COCHCOCH_3)$; $(CH_3)_2Au(C_6H5COCHCOCF_3)$; $CH_3AuP(CH_3)_3$; $AuP(CH_3)_3Cl$; $AuP(CH_3)_3NO_3$; $Au(PPh_3)NO_3$; $AuCH_3(PPh_3)$; $AuCl(PPh_3)$; $Au_2(CH_3)_6$; $Au(CH_3)_6(PPh_3)$.

The solvent used in Step A is not particularly limited as long as it can dissolves the foregoing gold compounds. Concretely, examples of the solvents include alcohols, ketones, ethers, esters, and hydrocarbons. Examples of alcohols include methyl alcohol, ethyl alcohol, isopropyl alcohol, n-butyl alcohol, octyl alcohol, and ethylene glycol. Examples of ketones include acetone, and methylethylketone, methylisobutylketone. Examples of ethers include tetrahydrofuran, and diisobutylether. Examples of esters include ethyl acetate, butyl acetate, and methyl propyonate. Examples of hydrocarbons include hexane, toluene, and xylene.

The concentration of the gold compound in the solution is not particularly limited, but preferably in a range of 0.01 mmol/L to 100 mmol/L in the case where the foregoing impregnation method or immersion method is adopted.

In the foregoing Step B, a heat treatment (calcination) is applied to the gold-containing solid substance obtained through the foregoing Step A, and a gold compound adhering to or bonded with the carrier is fixed to the carrier as gold fine particles. As a result, an epoxide-production-use catalyst in accordance with the present invention is produced.

Conditions of the calcination with respect to the gold-containing solid substance are not particularly limited, but the temperature is preferably in a range of 50° C. to 800° C., while the calcination time is in a range of 1 hour to 24 hours. To completely remove the solvent from the gold-containing solid substance obtained through the foregoing Step A, the solid compound can be dried before subjected to Step B.

The method for producing epoxides in accordance with the present invention, that is, the reaction style of partial oxidation of an unsaturated hydrocarbon with use of the epoxide-production-use catalyst thus arranged as above (epoxidation reaction) is not particularly limited, and it may be of the fixed bed type, the fluid bed type, or the moving bed type. The foregoing reaction is preferably carried out in gas phase, but is possibly carried out in liquid phase as well. In the following description, a case in which the reaction is carried out in gas phase is taken as an example.

The unsaturated hydrocarbon used as row material in the foregoing producing process is not particularly limited as long as it is a chemical compound having an olefinic double bond, but it is preferably a compound having 3 to 12 carbon atoms. Examples of such unsaturated hydrocarbons include olefins such as propylene, 1-butene, 2-butene, isobutene, 1-pentene, 2-pentene, 2-methyl-1-butene, 3-methyl-1-butene, cyclopentene, 1-hexene, 2-hexene, 3-hexene, 2-methyl-1-pentene, 3-methyl-1-pentene, 4-methyl-1-pentene, cyclohexene, 1-methyl-1-cyclopentene, and 3-methyl-1-cyclopentene. By partial oxidation of the olefinic double bond of the unsaturated hydrocarbon, an epoxide corresponding to the unsaturated hydrocarbon is produced.

The usage of the epoxide-production-use catalyst may be appropriately set depending on the amount of the gold fine particles carried thereon, the type of the unsaturated hydrocarbon, and the reaction conditions, and are not particularly limited. However, it is preferably set so that a space velocity (SV) of the unsaturated hydrocarbon upon reaction should be in a range of 100 $hr^{-1}$ ·ml/g·cat. to 10,000 $hr^{-1}$·ml/g·cat. (space velocity per 1 g of catalyst).

The reducing substance, though not particularly limited, is preferably at least one kind selected from among the group consisting of hydrogen, carbon monoxide, nitrogen monoxide, dinitrogen monoxide, alcohols, aldehydes, phenols, formic acids, oxalic acids, and cyclohexadienes. Hydrogen is particularly preferable.

The usage of the reducing substance, though not particularly limited, is preferably such that a volumetric ratio of the reducing substance to the unsaturated hydrocarbon (reducing substance/unsaturated hydrocarbon) should be in a range of 1/10 to 100/1. Since the reaction velocity increases as the amount of the reducing substance increases, the volumetric ratio is preferably as approximate to 100/1 as possible. The presence of the reducing substance in the reaction system ensures that the formation of epoxide takes place even at a low temperature such as not higher than 50° C. Incidentally, without the presence of a reducing substance in the reaction system, a reaction of the unsaturated hydrocarbon occurs at a temperature not lower than 200° C., hardly producing an epoxide but being completely oxidized to carbon dioxide and water.

The usage of oxygen, though not particularly limited, is preferably such that a volumetric ratio between oxygen and an unsaturated hydrocarbon (oxygen/unsaturated hydrocarbon) should be in a range of 1/10 to 10/1. Usage of oxygen smaller than the foregoing range is not preferable since in such a case the yield of epoxide lowers. On the other hand, an increase in the usage of oxygen so as to exceed the foregoing range is not preferable, since with such an increase, any improvement of the yield of an epoxide cannot be expected, while the selectivity lowers.

In the epoxide producing method in accordance with the present invention, partial oxidation of an unsaturated hydrocarbon is promoted by bringing row material gas including the unsaturated hydrocarbon, a reducing substance such as hydrogen, and oxygen into contact with an epoxide-production-use catalyst in accordance with the present invention. Therefore, preferable as a reaction method is a method in which the epoxide-production-use catalyst is filled in a reaction device and the foregoing row material gas is flown through the foregoing reaction device. By the foregoing method, a gas containing a target epoxide is produced. The row material gas may be diluted with an inert gas such as nitrogen, helium, argon, or carbon dioxide as required. The usage of the inert gas is not particularly limited. Incidentally, the type of reaction is not particularly limited, but the continuous type is preferable since the foregoing reaction is a gas-phase heterogeneous catalyst reaction.

The reaction temperature may be set according to the type of the unsaturated hydrocarbon, its combination with an epoxide-production-use catalyst, etc. and is not particularly limited. However, it is preferably set so that the unsaturated hydrocarbon and the epoxide can remain in gas phase, that is, in a range of 0° C. to 350° C., for instance, or more preferably in a range of 20° C. to 280° C. An excessively low reaction temperature is not preferable since it causes the yield of the epoxide to lower. On the other hand, an excessively high reaction temperature is not preferable, either, since it causes complete oxidation of the unsaturated hydrocarbon and epoxide, thereby producing carbon dioxide and water, resulting in that the selectivity of the epoxide lowers and that a quantity of a reducing substance consumed upon combustion increases.

The reaction pressure is not particularly limited and may be set according to the reaction conditions such as the reaction temperature, but it is preferably set so that the unsaturated hydrocarbon and the epoxide can remain in gas phase, that is, in a range of 0.01 MPa to 2 MPa, for instance. An excessively low reaction pressure is not preferable since it causes the yield of the epoxide to lower. On the other hand, an excessively high reaction pressure, though causing the yield of the epoxide to increase, is not practical (industrial) since in such a case an equipment such as compressor is required. The reaction time may be set according to reaction conditions such as a reaction temperature or a reaction pressure, and is not particularly limited.

In the epoxide producing method in accordance with the present invention, direct oxidation in gas phase, that is, gas-phase oxidation reaction, requires only a single step (single stage) of the reaction process. This enables obtainment of an epoxide from an unsaturated hydrocarbon with a high yield and a high selectivity (high conversion), as well as decrease of the amount of the reducing substance thus combusted. Consequently, the amount of the reducing substance consumed can be reduced as compared with that in the case of the conventional method. In short, the present invention can provide a method whereby an epoxide is obtained from an unsaturated hydrocarbon with a high yield and a high selectivity.

Incidentally, in the case where the reaction of partial oxidation of an unsaturated hydrocarbon is carried out in liquid phase, various types of reaction including the batch type, the semi-batch type, and the continuous flow type are adoptable. The reaction temperature and pressure in the liquid-phase reaction are preferably set so that the unsaturated hydrocarbon and the epoxide can remain in gas phase, that is, not higher than 150° C. with regard to the temperature and in a range of 0.05 MPa to 10 MPa with regard to the pressure.

Alternatively, an inert solvent with respect to the reaction may be used so that the foregoing reaction should be carried out in liquid phase. Applicable as a reaction method using a solvent is a method in which the aforementioned row material gas is bubbled in a suspension obtained by suspending the epoxide-production-use catalyst in accordance with the present invention in a solvent. Examples of the foregoing solvents include aromatic hydrocarbons such as benzene, etc., and halogenized hydrocarbons such as methylene chloride, etc., though not particularly limited. The usage of the solvent is not particularly limited.

The following description will explain the present invention in more detail, with examples and comparative examples. The present invention, however, is not limited by the following description at all.

EXAMPLE 1

60 g of silicon oxide (SILICA Q-10 (trade name) available from Fuji Silysia Chemical Ltd., with specific surface area of 326 m$^2$/g, 10 mesh to 20 mesh, particle diameter of 840 μm to 1700 μm,) as a support was immersed in 500 ml of a methyl alcohol solution containing 2.96 g of titanium (II) oxide acetylacetonate, 0.36 g of 30 wt % kalium methoxide methyl alcohol solution, and 0.07 g of sodium methoxide, and subsequently, methyl alcohol was removed by means of an evaporator.

A solid remaining substance obtained was dried at 120° C. for 12 hours and calcined at 600° C. for 3 hours in air atmosphere, whereby a carrier (titanium-oxide-carrying silicon oxide) A in the present invention was obtained. Loadings of titanium oxide (titania: titanium-containing oxide) to the carrier A (hereinafter referred to as amount of loadings as required) was 1.5 wt % (mass). According to analysis of loadings of sodium (alkaline metal element) and kalium (alkaline metal element) in the carrier A by the fluorescent X-ray method, the amounts of sodium and kalium were 0.05 wt % and 0.1 wt % in terms of metal, respectively. Furthermore, an acid quantity of the carrier A measured by the aforementioned NH$_3$-TPD method was 0.067 mmol/g, which satisfied the requirement that the acid quantity should be not more than 0.15 mmol/g.

Next, 50 g of the carrier A was immersed in 100 ml of a methyl alcohol solution dissolving 0.0326 g (0.10 mmol) of dimethyl gold acetylacetonate, and methyl alcohol was removed by means of an evaporator at normal pressure. Subsequently, a gold-containing solid substance was calcined at 300° C. for 3 hours in air atmosphere, so that a catalyst (Au—Na—K—Ti—SiO$_2$) in which gold fine particles were carried on (fixed to) the carrier A was obtained. The amount of loadings of gold in this catalyst was analyzed by the fluorescent X-ray method, and it was found to be 0.04 wt % in terms of metal. Furthermore, an acid quantity of the catalyst measured by the aforementioned NH$_3$-TPD method was 0.043 mmol/g. Thus, it was confirmed that the obtained catalyst was an epoxide-production-use catalyst in accordance with the present invention (hereinafter referred to as catalyst A).

Subsequently, 2.5 ml(cc) of the foregoing catalyst A was filled in a tube reactor with an inner diameter of 10 mm, and a row material gas was flown therethrough at flow rate of 5,000 hr$^{-1}$·ml/g·cat. (equivalent value at normal temperature under normal pressure) while the temperature of the catalyst layer was maintained at 200° C., so that epoxidation of propylene was carried out. Note that the foregoing row material gas was a mixture gas containing hydrogen, oxygen, propylene, and argon at volumetric ratio (hydrogen/oxygen/propylene/argon) of 20/20/20/40.

Then, at 0.5 hour, 50 hours, 100 hours, and 500 hours after the reaction start, gas at an outlet of the tube reactor was sampled, and its composition was analyzed by gas chromatography, so that variation of a yield (yield A) of propylene oxide (epoxide) with time was inspected. The measurement result of the acid quantity with regard to the catalyst A and the yield A is shown in Table 1.

Fresh catalyst A was prepared separately, and the epoxidation reaction of propylene was carried out to continue for 500 hours with use of this catalyst A under the same conditions as those described above. After the reaction, the catalyst A was taken out of the reaction system and subjected to a heat treatment (regenerating operation) at 280° C. for 30 minutes with use of a mixture gas containing oxygen and helium at a volumetric ratio of 9:91, so that the catalyst activity should be recovered.

Subsequently, the epoxidation reaction of propylene was again carried out under the same conditions as those described above except that the catalyst A thus having been subjected to the heat treatment was used. Yields of propylene oxide (yields A') at 0.5 hours, 50 hours, 100 hours, and 500 hours after the reaction start were 3.3%, 2.7%, 2.3%, and 1.9%, respectively. In other words, all the regenerating rates of the catalyst A in accordance with the present invention (yield A'/yield A×100(%)) were in a range of 80% to 100%, and this shows that it was possible to recover the catalyst activity to a level sufficient for practical application, by the regenerating operation.

Comparative Example 1

After 60 g of silicon oxide (same as that in Example 1) was immersed in 500 ml of a methyl alcohol solution containing 2.96 g of titanium (II) oxide acetylacetonate, methyl alcohol was removed by means of an evaporator.

A solid remaining substance obtained was dried at 120° C. for 12 hours and calcined at 400° C. for 3 hours in air atmosphere, whereby a carrier (1) was obtained. An amount of loadings of titanium oxide (titania) on the carrier (1) was 1.5 wt %. Further, an acid quantity of the carrier (1) measured by the aforementioned NH$_3$-TPD method was 0.153 mmol/g, which did not satisfy the requirement that the acid quantity should be not more than 0.15 mmol/g.

Next, gold fine particles were fixed to the carrier (1) in the same manner that was used in Example 1 except that the carrier (1) was used in place of the carrier A, and a comparative catalyst (1) was obtained. The loadings of gold, sodium, and kalium in the comparative catalyst (1) were analyzed by the fluorescent X-ray method, and it was found that the amount of gold was 0.04 wt % in terms of metal, while no sodium and kalium was detected. Furthermore, an acid quantity of the comparative catalyst (1) measured by the aforementioned NH$_3$-TPD method was 0.12 mmol/g, exceeding 0.1 mmol/g.

Subsequently, the epoxidation of propylene was carried out under the same conditions as those in Example 1 except that the comparative catalyst (1) was used in place of the catalyst A, and variation of the yield of propylene oxide with time was inspected. Measurement results of the acid quantity of the comparative catalyst (1) and the yield of propylene oxide are shown in Table 1.

Fresh comparative catalyst (1) was prepared separately, and the epoxidation reaction of propylene was carried out for 500 hours with use of this comparative catalyst (1) under the same conditions as those described above. After the reaction, the comparative catalyst (1) was taken out of the reaction system and subjected to a heat application at 280° C. for 30 minutes with use of a mixture gas containing oxygen and helium at a volumetric ratio of 9:91, so that the catalyst activity should be recovered.

Subsequently, the epoxidation reaction of propylene was again carried out under the same conditions as those described above except that the comparative catalyst (1) thus having been subjected to the heat treatment was used. Yields of propylene oxide at 0.5 hours, 50 hours, 100 hours, and 500 hours after the reaction start were 2.7%, 1.8%, 1.3%, and 0.4%, respectively. In other words, all the recycle rates of the comparative catalyst (1) were in the order of 60%, and this shows that it was impossible to recover the catalyst activity to a level sufficient for practical application, by the recycling operation.

EXAMPLE 2

A carrier B in the present invention was prepared in the same manner as that in Example 1 except that 500 ml of methyl alcohol solution containing 2.96 g of titanium (II) oxide acetylacetonate, 0.47 g of zirconium (IV) acetylacetonate, 0.36 g of 30 wt % kalium methoxide methyl alcohol solution, and 0.07 g of sodium methoxide was used as the solution in which silicon oxide was immersed.

An amount of loadings of titanium oxide (titania: titanium-containing oxide) on the carrier B was 1.5 wt %, while an amount of loadings of zirconium oxide (zirconia:zirconium-containing oxide) on the carrier B was 0.2 wt %. Furthermore, amounts of loadings of sodium (alkaline metal element) and kalium (alkaline metal element) on the carrier B were 0.05 wt % and 0.1 wt % in terms of metal, respectively. Furthermore, an acid quantity of the carrier B measured by the aforementioned $NH_3$-TPD method was 0.143 mmol/g, which satisfied the requirement that the acid quantity should be not more than 0.15 mmol/g.

Next, a catalyst (Au—Na—K—Ti—Zr—$SiO_2$) in which gold fine particles were fixed to the carrier B was obtained in the same manner as that in Example 1 except that the carrier B was used in place of the carrier A. An amount of loadings of gold in this catalyst was analyzed by the fluorescent X-ray method, and it was found to be 0.04 wt % in terms of metal. Furthermore, an acid quantity of the catalyst measured by the aforementioned $NH_3$-TPD method was 0.093 mmol/g. Thus, it was confirmed that the obtained catalyst was an epoxide-production-use catalyst in accordance with the present invention (hereinafter referred to as catalyst B).

Subsequently, the epoxidation reaction of propylene was carried out under the same conditions as those in Example 1 except that the catalyst B was used in place of the catalyst A, and variation of the yield of propylene oxide with time was inspected. Measurement results of the acid quantity of the catalyst B and the yield are shown in Table 1.

Fresh catalyst B was prepared separately, and the epoxidation reaction of propylene was carried out to continue for 500 hours with use of this catalyst B under the same conditions as those described above. After the reaction, the catalyst B was taken out of the reaction system and was subjected to a heat application at 280° C. for 30 minutes with use of a mixture gas containing oxygen and helium at a volumetric ratio of 9:91, so that the catalyst activity should be recovered.

Subsequently, the epoxidation reaction of propylene was again carried out under the same conditions as those described above except that the catalyst B thus having been subjected to the heat treatment was used. Yields of propylene oxide at 0.5 hours, 50 hours, 100 hours, and 500 hours after the reaction start were 2.7%, 2.3%, 1.9%, and 1.6%, respectively. In other words, all the recycle rates of the catalyst B were in the range of 80% to 100%, and this shows that it was possible to recover the catalyst activity to a level sufficient for practical application, by the recycling operation.

Comparative Example 2

A carrier (2) was prepared in the same manner as that in Example 1 except that 500 ml of methyl alcohol solution containing 2.96 g of titanium (II) oxide acetylacetonate, 0.47 g of zirconium (IV) acetylacetonate was used as the solution in which silicon oxide was immersed. An acid quantity of the carrier (2) measured by the aforementioned $NH_3$-TPD method was 0.165 mmol/g, which did not satisfy the requirement that the acid quantity should be not more than 0.15 mmol/g.

Next, gold fine particles were fixed to the carrier (2) in the same manner as that in Example 1 except that the carrier (2) was used in place of the carrier A, and a comparative catalyst (2) was obtained. An acid quantity of the comparative catalyst (2) was found to be 0.153 mmol/g, exceeding 0.1 mmol/g.

Subsequently, the epoxidation reaction of propylene was carried out under the same conditions as those in Example 1 except that the comparative catalyst (2) was used in place of the catalyst A, and variation of the yield of propylene oxide with time was inspected. Measurement results of the acid quantity of the comparative catalyst (2) and the yield of propylene oxide are shown in Table 1.

Fresh comparative catalyst (2) was prepared separately, and the epoxidation reaction of propylene was carried out to continue for 500 hours with use of this comparative catalyst (2) under the same conditions as those described above. After the reaction, the comparative catalyst (2) was taken out of the reaction system and was subjected to a heat application at 280° C. for 30 minutes with use of a mixture gas containing oxygen and helium at a volumetric ratio of 9:91, so that the catalyst activity should be recovered.

Subsequently, the epoxidation reaction of propylene was again carried out under the same conditions as those described above except that the comparative catalyst (2) thus having been subjected to the heat treatment was used. Yields of propylene oxide at 0.5 hours, 50 hours, 100 hours, and 500 hours after the reaction start were 1.3%, 1.0%, 0.5%, and 0.3%, respectively. In other words, the recycle rate of the comparative catalyst (2), particularly after 0.5 hour, was in the order of 50%, and this shows that it was impossible to recover the catalyst activity to a level sufficient for practical application, by the recycling operation.

EXAMPLE 3

The carrier (2) in the foregoing Comparative Example 2 was immersed in methyl alcohol, and was heated at 64° C. in reflux for 30 minutes. Subsequently, the carrier (2) thus processed was dried at 120° C. and then subjected to a heat treatment at 250° C. for 30 minutes in air atmosphere, whereby a carrier C was obtained (contact nd heat treatment). An acid quantity of the carrier C measured by the aforementioned $NH_3$-TPD method was 0.13 mmol/g, which satisfied the requirement that the acid quantity should be not more than 0.15 mmol/g.

Next, a catalyst in which gold fine particles were fixed to the carrier C was obtained in the same manner as that in Example 1 except that the carrier C was used in place of the carrier A. An acid quantity of the catalyst measured by the aforementioned $NH_3$-TPD method was 0.096 mmol/g. Thus, it was confirmed that the obtained catalyst was an epoxide-production-use catalyst in accordance with the present invention (hereinafter referred to as catalyst C).

Subsequently, the epoxidation reaction of propylene was carried out under the same conditions as those in Example 1 except that the catalyst C was used in place of the catalyst A, and variation of the yield of propylene oxide with time was inspected. Measurement results of the acid quantity of the catalyst C and the yield of propylene oxide are shown in Table 1.

Fresh catalyst C was prepared separately, and the epoxidation reaction of propylene was carried out to continue for 500 hours with use of this catalyst C under the same conditions as those described above. After the reaction, the catalyst C was taken out of the reaction system and subjected to a heat application at 280° C. for 30 minutes with use of a mixture gas containing oxygen and helium at a volumetric ratio of 9:91, so that the catalyst activity should be recovered.

Subsequently, the epoxidation reaction of propylene was again carried out under the same conditions as those described above except that the catalyst C thus having been subjected to the heat treatment was used. Yields of propylene oxide at 0.5 hours, 50 hours, 100 hours, and 500 hours after the reaction start were 2.3%, 2.0%, 1.2%, and 0.9%, respectively. In other words, all the recycle rates of the catalyst C were in the range of 80% to 100%, and this shows that it was possible to recover the catalyst activity to a level sufficient for practical application, by the recycling operation.

EXAMPLE 4

After 60 g of silicon oxide (same as that in Example 1) was immersed in 250 ml of methyl alcohol solution containing 3.94 g of titanium (II) oxide acetylacetonate, methyl alcohol was removed by evaporation.

A solid remaining substance obtained was dried at 120° C. for 12 hours and calcined at 400° C. for 3 hours in air atmosphere, whereby a carrier before acid quantity adjustment was obtained. An amount of loadings of titanium oxide (titania:titanium-containing oxide) on the carrier (1) was 20 wt %. Further, an acid quantity of the carrier measured by the aforementioned $NH_3$-TPD method was 0.17 mmol/g.

Subsequently, 20 g of the foregoing carrier was filled in a stainless steel pipe, and argon gas containing methoxymethylsilane (silylating reagent) vapor at a ratio of about 10 percent by volume (vol %) was flown therethrough at flow rate of 5,000 $hr^{-1}$·ml (per 1 g of titanium-containing oxide) while the temperature was maintained at 200° C., so that silylation of the carrier was practiced. In the carrier after the silylation (carrier D in the present invention), a weight increase by 2.6 wt % was recognized. It had an acid quantity of 0.01 mmol/g, which satisfied the requirement that the acid quantity should be not more than 0.15 mmol/g.

Then, 150 ml of methyl alcohol solution dissolving therein 0.0326 g (0.10 mmol) of dimethyl gold acetylacetonate as a gold compound was maintained at 40° C., in which the totality of the carrier D was soaked. Subsequently, the methyl alcohol solution was filtered, so that a gold-containing solid substance was filtered out.

Subsequently, the gold-containing solid substance thus obtained was calcined at 300° C. for 3 hours in air atmosphere, whereby a catalyst (Au—Ti—$SiO_2$) in which gold fine particles are carried on the carrier D was obtained. An amount of loadings of gold in this catalyst was analyzed by the fluorescent X-ray method, and it was found to be 0.1 wt % in terms of metal. Furthermore, an acid quantity of the catalyst measured by the aforementioned $NH_3$-TPD method was 0.082 mmol/g. Thus, it was confirmed that the obtained catalyst was an epoxide-production-use catalyst in accordance with the present invention (hereinafter referred to as catalyst D).

Next, 2.5 ml of the foregoing catalyst D was filled in the tube reactor, and a row material gas was flown therethrough at flow rate of 5,000 $hr^{-1}$·ml/g·cat. (equivalent value at normal temperature under normal pressure) for 10 minutes while the temperature of the catalyst layer was maintained at 210° C., so that epoxidation of trans-2-butene was carried out. Note that the foregoing row material gas was a mixture gas containing hydrogen, oxygen, trans-2-butene, and argon at volumetric ratio (hydrogen/oxygen/trans-2-butene/argon) of 20/20/20/40.

Then, at 0.5 hour, 50 hours, 100 hours, and 500 hours after the reaction start, gas at an outlet of the tube reactor was sampled, and its composition was analyzed by gas chromatography, so that variation of a yield (yield B) of 2,3-epoxybutane (epoxide) with time was inspected. Measurement results of the acid quantity of the catalyst D and the yield of 2,3-epoxybutane are shown in Table 1.

Fresh catalyst D was prepared separately, and the epoxidation reaction of trans-2-butene was carried out to continue for 500 hours with use of this catalyst D under the same conditions as those described above. After the reaction, the catalyst D was taken out of the reaction system and was subjected to a heat application at 280° C. for 30 minutes with use of a mixture gas containing oxygen and helium at a volumetric ratio of 9:91, so that the catalyst activity should be recovered.

Subsequently, the epoxidation reaction of trans-2-butene was again carried out under the same conditions as those described above except that the catalyst D thus having been subjected to the heat treatment was used. Yields of 2,3-epoxybutane (yields B') at 0.5 hours, 50 hours, 100 hours, and 500 hours after the reaction start were 4.1%, 3.8%, 3.5%, and 2.9%, respectively. In other words, all the recycle rates of the catalyst D in accordance with the present invention (yield B'/yield B×100(%)) were in a range of 90% to 100%, and this shows that it was possible to recover the catalyst activity to a level sufficient for practical application, by the recycling operation.

Comparative Example 3

A comparative catalyst (3) was obtained in the same manner as that in Example 4 except that a carrier before silylated was used as carrier (3), to which gold fine particles were fixed. An acid quantity of the comparative catalyst (3) was 0.13 mmol/g, exceeding 0.1 mmol/g.

Subsequently, the epoxidation reaction of trans-2-butene was carried out under the same conditions as those in Example 4 except that the comparative catalyst (3) was used in place of the catalyst D, and variation of the yield of 2,3-epoxybutane with time was inspected. Measurement results of the acid quantity of the comparative catalyst (3) and the yield of 2,3-epoxybutane are shown in Table 1.

Fresh comparative catalyst (3) was prepared separately, and the epoxidation reaction of trans-2-butene was carried out for 500 hours with use of this catalyst (3) under the same conditions as those described above. After the reaction, the comparative catalyst (3) was taken out of the reaction system and subjected to a heat application at 280° C. for 30 minutes with use of a mixture gas containing oxygen and helium at a volumetric ratio of 9:91, so that the catalyst activity should be recovered.

subsequently, the epoxidation reaction of trans-2-butene was again carried out under the same conditions as those described above except that the comparative catalyst (3) thus having been subjected to the heat treatment was used. Yields of 2,3-epoxybutane at 0.5 hours, 50 hours, 100 hours, and 500 hours after the reaction start were 2.8%, 1.8%, 1.3%, and 0.8%, respectively. In other words, all the recycle rates of the comparative catalyst (3) lowered with time, to less than 60% after use over 500 hours in particular. This shows that it was impossible to recover the catalyst activity to a level sufficient for practical application, by the recycling operation.

EXAMPLE 5

A carrier was prepared in the same manner as that in Example 4 except that the carrier before acid quantity adjustment was processed with use of pyridine as charge-supply compound instead of being silylated. The foregoing processing operation with use of pyridine (pyridine processing) was an operation in which 20 g of the foregoing carrier was filled in a stainless steel pipe and was maintained at 200° C., and argon gas containing pyridine vapor at a rate of about 0.57 vol % was flown therethrough (brought into contact therewith) at flow rate of 5,000 $hr^{-1}$·ml (per 1 g of titanium-containing oxide) for 10 minutes. The carrier after subjected to the foregoing pyridine processing operation (carrier E in the present invention) had an acid quantity of 0.09 mmol/g, which satisfied the requirement that the acid quantity should be not more than 0.15 mmol/g.

Subsequently, a catalyst in which gold fine particles were fixed to the carrier E was obtained in the same manner as that in Example 4 except that the carrier E was used in place of the carrier D. An acid quantity of the catalyst measured by the aforementioned $NH_3$-TPD method was 0.075 mmol/g. Thus, it was confirmed that the obtained catalyst was an epoxide-production-use catalyst in accordance with the present invention (hereinafter referred to as catalyst E).

Subsequently, the epoxidation reaction of trans-2-butene was carried out under the same conditions as those in Example 4 except that the catalyst E was used in place of the catalyst D, and variation of the yield of 2,3-epoxybutane with time was inspected. Measurement results of the acid quantity of the catalyst E and the yield of 2,3-epoxybutane are shown in Table 2.

Fresh catalyst E was prepared separately, and the epoxidation reaction of trans-2-butene was carried out for 500 hours with use of this catalyst E under the same conditions as those described above. After the reaction, the catalyst E was taken out of the reaction system and subjected to a heat application at 280° C. for 30 minutes with use of a mixture gas containing oxygen and helium at a volumetric ratio of 9:91, so that the catalyst activity should be recovered.

Subsequently, the epoxidation reaction of trans-2-butene was again carried out under the same conditions as those described above except that the catalyst E thus having been subjected to the heat treatment was used. Yields of 2,3-epoxybutane at 0.5 hours, 50 hours, 100 hours, and 500 hours after the reaction start were 3.3%, 3.1%, 2.7%, and 2.0%, respectively. In other words, all the recycle rates of the catalyst E in accordance with the present invention were in a range of 80% to 100%, and this shows that it was possible to recover the catalyst activity to a level sufficient for practical application, by the recycling operation.

EXAMPLE 6

A solid remaining substance obtained by the carrier (1) preparing method of the above-described Comparative Example 1 was dried at 120° C. for 12 hours and calcined under calcination conditions of "a temperature of 950° C., a calcination period of 3 hours, surroundings of air atmosphere" (high-temperature calcination process), whereby a carrier F was obtained. An amount of loadings of titanium oxide (titania: titanium-containing oxide) on the carrier F was 1.5 wt %. Further, an acid quantity of the carrier F measured by the aforementioned $NH_3$-TPD method was 0.07 mmol/g, which satisfied the requirement that the acid quantity should be not more than 0.15 mmol/g.

Subsequently, a catalyst in which gold fine particles were fixed to the carrier F was obtained in the same manner as that in Comparative Example 1 except that the carrier F was used in place of the carrier (1). An acid quantity of the catalyst measured by the aforementioned $NH_3$-TPD method was 0.06 mmol/g. Thus, it was confirmed that the obtained catalyst was an epoxide-production-use catalyst in accordance with the present invention.

Subsequently, the epoxidation reaction of propylene was carried out under the same conditions as those in Example 1 except that the catalyst F was used in place of the catalyst A, and variation of the yield of propylene oxide with time was inspected. Measurement results of the acid quantity of the catalyst F and the yield of propylene oxide are shown in Table 2.

Fresh catalyst F was prepared separately, and the epoxidation reaction of propylene was carried out to continue for 500 hours with use of this catalyst F under the same conditions as those described above. After the reaction, the catalyst F was taken out of the reaction system and subjected to a heat application at 280° C. for 30 minutes with use of a mixture gas containing oxygen and helium at a volumetric ratio of 9:91, so that the catalyst activity should be recovered.

Subsequently, the epoxidation reaction of propylene was again carried out under the same conditions as those described above except that the catalyst F thus having been subjected to the heat treatment was used. Yields of propylene oxide at 0.5 hours, 50 hours, 100 hours, and 500 hours after the reaction start were 3.6%, 2.5%, 2.2%, and 1.2%, respectively. In other words, all the recycle rates of the catalyst F were in the range of 90% to 100%, and this shows that it was possible to recover the catalyst activity to a level sufficient for practical application, by the recycling operation.

EXAMPLE 7

60 g of silicon oxide (same as that in Example 1) was immersed for 10 minutes in 50 ml of a methyl alcohol solution containing 1.06 g of tetraisopropyltitanate, 0.07 g of sodium methoxide, 0.02 g of molybdenum oxide acetylacetonate, 0.2 g of vanadium oxide acetylacetonate, 0.24 g of aluminum acetylacetonate, 1.28 of magnesium acetylacetonate, and 1.5 g of acetylacetone, then, methyl alcohol was removed by evaporation under reduced pressure.

A solid remaining substance obtained was dried at 120° C. for 12 hours and calcined at 400° C. for 6 hours in air atmosphere, whereby a carrier G in the present invention was obtained. An amount (amount of loadings) of titanium oxide (titania: titanium-containing oxide) in the carrier G was 0.5 wt %. Amounts of loadings of sodium (alkaline metal element), magnesium (alkaline earth metal element), molybdenum, vanadium, and aluminum in the carrier G were analyzed by the fluorescent X-ray method, and they were found to be 0.05 wt %, 0.2 wt %, 0.01 wt %, 0.06 wt %, 0.03 wt %, and 0.03 wt % in terms of metal, respectively. Further, an acid quantity of the carrier G measured by the aforementioned $NH_3$-TPD method was 0.062 mmol/g, which did not satisfy the requirement that the acid quantity should be not more than 0.15 mmol/g.

Subsequently, the carrier G was immersed in 100 ml of a methyl alcohol solution dissolving 0.0489 g (0.15 mmol) of dimetyl gold acetylacetonate as a gold compound, and methyl alcohol was removed by evaporation by means of an evaporator under normal pressure. Then, a gold-containing solid substance obtained was calcined at 300° C. for 3 hours in air atmosphere, whereby a catalyst in which gold fine particles are carried on the carrier G (Au—V—Al—Na—Mg—Ti—$SiO_2$) was obtained. An amount of loadings of gold in this catalyst was analyzed by the fluorescent X-ray method, and it was found to be 0.06 wt % in terms of metal. Furthermore, an acid quantity of the catalyst measured by the aforementioned $NH_3$-TPD method was 0.058 mmol/g. Thus, it was confirmed that the obtained catalyst was an epoxide-production-use catalyst in accordance with the present invention (hereinafter referred to as catalyst G).

Subsequently, the epoxidation reaction of propylene was carried out under the same conditions as those in Example 1 except that the catalyst G was used in place of the catalyst A, and variation of the yield of propylene oxide with time was inspected. Measurement results of the acid quantity of the catalyst G and the yield of propylene oxide are shown in Table 2.

Fresh catalyst G was prepared separately, and the epoxidation reaction of propylene was carried out to continue for 500 hours with use of this catalyst G under the same conditions as those described above. After the reaction, the catalyst G was taken out of the reaction system and subjected to a heat application at 280° C. for 30 minutes with use of a mixture gas containing oxygen and helium at a volumetric ratio of 9:91, so that the catalyst activity should be recovered.

Subsequently, the epoxidation reaction of propylene was again carried out under the same conditions as those described above except that the catalyst G thus having been subjected to the heat treatment was used. Yields of propylene oxide at 0.5 hours, 50 hours, 100 hours, and 500 hours after the reaction start were 2.9%, 2.6%, 1.7%, and 1.1%, respectively. In other words, all the recycle rates of the catalyst G were in the range of 80% to 95%, and this shows that it was possible to recover the catalyst activity to a level sufficient for practical application, by the recycling operation.

Comparative Example 4

A carrier (4) was prepared in the same manner as that in Example 7 except that 50 ml of a methyl alcohol solution containing 1.06 g of tetraisopropyltitanate, 0.02 g of molybdenum oxide acetylacetonate, 0.2 g of vanadium oxide acetylacetonate, 0.24 g of aluminum acetylacetonate, and 1.5 g of acetylacetone was used as the solution in which silicon oxide was to be immersed. The carrier (4) had an acid quantity of 0.18 mmol/g, that exceeded 0.15 mmol/g.

Subsequently, gold fine particles were fixed to the carrier (4) in the same manner that was used in Example 7 except that the carrier (4) was used in place of the carrier G, and a comparative catalyst (4) was obtained. An acid quantity of the comparative catalyst (4) was found to be 0.12 mmol/g, exceeding 0.1 mmol/g.

Subsequently, the epoxidation reaction of propylene was carried out under the same conditions as those in Example 1 except that the comparative catalyst (4) was used in place of the catalyst A, and variation of the yield of propylene oxide with time was inspected. Measurement results of the acid quantity of the comparative catalyst (4) and the yield of propylene oxide are shown in Table 2.

Fresh comparative catalyst (4) was prepared separately, and the epoxidation reaction of propylene was carried out to continue for 500 hours with use of this comparative catalyst (4) under the same conditions as those described above. After the reaction, the comparative catalyst (4) was taken out of the reaction system and subjected to a heat application at 280° C. for 30 minutes with use of a mixture gas containing oxygen and helium at a volumetric ratio of 9:91, so that the catalyst activity should be recovered.

Subsequently, the epoxidation reaction of propylene was again carried out under the same conditions as those described above except that the comparative catalyst (4) thus having been subjected to the heat treatment was used. Yields of propylene oxide at 0.5 hours, 50 hours, 100 hours, and 500 hours after the reaction start were 1.8%, 1.2%, 0.5%, and 0.4%, respectively. In other words, all the recycle rates of the comparative catalyst (4) were less than 67%, and this shows that it was impossible to recover the catalyst activity to a level sufficient for practical application, by the recycling operation.

EXAMPLE 8

60 g of silicon oxide (same as that in Example 1) was immersed for 10 minutes in 50 ml of a methyl alcohol solution dissolving 1.06 g of tetraisopropyltitanate, 0.03 g of iron thiocyanate, 0.05 g of acetylacetone ruthenium (III), 0.05 g of zinc (II) acetylacetonate, 0.1 g of tris(2,4-pentandinate)cerium (III) trihydrate, and 1.5 g of acetylacetone, then, methyl alcohol was removed by evaporation under reduced pressure.

A solid remaining substance obtained was dried at 120° C. for 12 hours and calcined at 400° C. for 6 hours in air atmosphere, whereby a carrier H in the present invention was obtained. An amount of loadings of titanium oxide (titania: titanium-containing oxide) in the carrier H was 0.5 wt %. Amounts of loadings of ruthenium, zinc, phosphorus, iron, and cerium (rare earth element) in the carrier H were analyzed by the fluorescent X-ray method, and they were found to be 0.02 wt %, 0.02 wt %, 0.019 wt %, 0.016 wt %, and 0.05 wt % in terms of metal, respectively. Further, an acid quantity of the carrier H measured by the aforementioned $NH_3$-TPD method was 0.083 mmol/g, which satisfied the requirement that the acid quantity should be not more than 0.15 mmol/g.

Subsequently, gold fine particles were fixed to the carrier H in the same manner as that in Example 7 except that the carrier H was used in place of the carrier G, and a catalyst H was obtained. An acid quantity of the catalyst H measured by the aforementioned $NH_3$-TPD method was 0.080 mmol/g. Thus, it was confirmed that the obtained catalyst was an epoxide-production-use catalyst in accordance with the present invention. An amount of loadings of gold in this catalyst H was found to be 0.06 wt % in terms of metal.

Next, 2.5 ml of the foregoing catalyst H was filled in a tube reactor with an inner diameter of 10 mm, and a row material gas was flown therethrough at flow rate of 5,000 $hr^{-1}$·ml/g·cat. (equivalent value at normal temperature under normal pressure) while the temperature of the catalyst layer was maintained at 200° C., so that epoxidation of cis-2-butene was carried out. Note that the foregoing row material gas was a mixture gas containing hydrogen, oxygen, cis-2-butene, and argon at volumetric ratio (hydrogen/oxygen/cis-2-butene/argon) of 20/20/20/40.

Then, at 0.5 hour, 50 hours, 100 hours, and 500 hours after the reaction start, gas at an outlet of the tube reactor was sampled, and its composition was analyzed by gas chromatography, so that variation of a yield (yield B) of 2,3-epoxybutane (epoxide) with time was inspected. Measurement results of the acid quantity of the catalyst H and the yield of 2,3-epoxybutane are shown in Table 2.

Fresh catalyst H was prepared separately, and the epoxidation reaction of cis-2-butene was carried out to continue for 500 hours with use of this catalyst H under the same conditions as those described above. After the reaction, the catalyst H was taken out of the reaction system and subjected to a heat application at 280° C. for 30 minutes with use of a mixture gas containing oxygen and helium at a volumetric ratio of 9:91, so that the catalyst activity should be recovered.

Subsequently, the epoxidation reaction of cis-2-butene was again carried out under the same conditions as those described above except that the catalyst H thus having been subjected to the heat treatment was used. Yields of 2,3-epoxybutane at 0.5 hours, 50 hours, 100 hours, and 500 hours after the reaction start were 3.4%, 2.5%, 2.1%, and 1.1%, respectively, and this shows that it was possible to recover the catalyst activity to a level sufficient for practical application, by the recycling operation.

Comparative Example 5

A carrier (5) was prepared in the same manner as that in Example 8 except that 50 ml of a methyl alcohol solution containing 1.06 g of tetraisopropyltitanate, 0.03 g of iron thiocyanate, 0.05 g of acetylacetone ruthenium (III), 0.05 g of zinc (II) acetylacetonate, and 1.5 g of acetylacetone was used as the solution into which silicon oxide was to be immersed. The carrier (5) had an acid quantity of 0.17 mmol/g, that exceeded 0.15 mmol/g.

Subsequently, gold fine particles were fixed to the carrier (5) in the same manner that was used in Example 8 except that the carrier (5) was used in place of the carrier H, and a comparative catalyst (5) was obtained. An acid quantity of the comparative catalyst (5) was found to be 0.17 mmol/g, exceeding 0.1 mmol/g.

Subsequently, the epoxidation reaction of cis-2-butene was carried out under the same conditions as those in Example 8 except that the comparative catalyst (5) was used in place of the catalyst H, and variation of the yield of 2,3-epoxybutane with time was inspected. Measurement results of the acid quantity of the comparative catalyst (5) and the yield of 2,3-epoxybutane are shown in Table 2.

Fresh comparative catalyst (5) was prepared separately, and the epoxidation reaction of cis-2-butene was carried out for 500 hours with use of this catalyst (5) under the same conditions as those described above. After the reaction, the comparative catalyst (5) was taken out of the reaction system and subjected to a heat application at 280° C. for 30 minutes with use of a mixture gas containing oxygen and helium at a volumetric ratio of 9:91, so that the catalyst activity should be recovered.

Subsequently, the epoxidation reaction of cis-2-butene was again carried out under the same conditions as those described above except that the comparative catalyst (5) thus having been subjected to the heat treatment was used. Yields of 2,3-epoxybutane at 0.5 hours, 50 hours, 100 hours, and 500 hours after the reaction start were 1.7%, 1.4%, 1.0%, and 0.6%, respectively. In other words, all the recycle rates of the comparative catalyst (5) were around 50%.

TABLE 1

| | ACID QUANTITY OF CATALYST (mmol/g) | UNSATURATED HYDROCARBON | EPOXIDE | REACTION TIME (hr) | YIELD (%) |
|---|---|---|---|---|---|
| EX. 1 | 0.43 | PROPYLENE | PROPYLENE OXIDE | 0.5 | 4.1 |
| | | | | 50 | 3.2 |
| | | | | 100 | 2.5 |
| | | | | 500 | 1.9 |
| COMP. EX. 2 | 0.12 | PROPYLENE | PROPYLENE OXIDE | 0.5 | 4.2 |
| | | | | 50 | 2.6 |
| | | | | 100 | 2.0 |
| | | | | 500 | 0.6 |
| EX. 2 | 0.093 | PROPYLENE | PROPYLENE OXIDE | 0.5 | 3.1 |
| | | | | 50 | 2.5 |
| | | | | 100 | 2.1 |
| | | | | 500 | 1.6 |
| COMP. EX. 2 | 0.153 | PROPYLENE | PROPYLENE OXIDE | 0.5 | 2.6 |
| | | | | 50 | 1.6 |
| | | | | 100 | 0.8 |
| | | | | 500 | 0.4 |
| EX. 3 | 0.096 | PROPYLENE | PROPYLENE OXIDE | 0.5 | 2.7 |
| | | | | 50 | 2.2 |
| | | | | 100 | 1.2 |
| | | | | 500 | 0.9 |
| EX. 4 | 0.082 | t-2-BUTENE | 2,3-BUTENE OXIDE (2,3-EPOXYBUTANE) | 0.5 | 4.5 |
| | | | | 50 | 4.0 |
| | | | | 100 | 3.5 |
| | | | | 500 | 2.9 |
| COMP. EX. 3 | 0.13 | t-2-BUTENE | 2,3-BUTENE OXIDE (2,3-EPOXYBUTANE) | 0.5 | 4.0 |
| | | | | 50 | 2.7 |
| | | | | 100 | 2.0 |
| | | | | 500 | 1.4 |

TABLE 2

| | ACID QUANTITY OF CATALYST (mmol/g) | UNSATURATED HYDROCARBON | EPOXIDE | REACTION TIME (hr) | YIELD (%) |
|---|---|---|---|---|---|
| EX. 5 | 0.075 | t-2-BUTENE | 2,3-BUTENE OXIDE (2,3-EPOXYBUTANE) | 0.5<br>50<br>100<br>500 | 4.0<br>3.2<br>2.7<br>2.0 |
| EX. 6 | 0.06 | PROPYLENE | PROPYLENE OXIDE | 0.5<br>50<br>100<br>500 | 4.0<br>2.7<br>2.3<br>1.3 |
| EX. 7 | 0.058 | PROPYLENE | PROPYLENE OXIDE | 0.5<br>50<br>100<br>500 | 3.6<br>3.0<br>1.9<br>1.2 |
| COMP. EX. 4 | 0.12 | PROPYLENE | PROPYLENE OXIDE | 0.5<br>50<br>100<br>500 | 3.5<br>2.1<br>1.0<br>0.6 |
| EX. 8 | 0.080 | c-2-BUTENE | 2,3-BUTENE OXIDE (2,3-EPOXYBUTANE) | 0.5<br>50<br>100<br>500 | 3.5<br>3.0<br>2.3<br>1.7 |
| COMP. EX. 5 | 0.17 | c-2-BUTENE | 2,3-BUTENE OXIDE (2,3-EPOXYBUTANE) | 0.5<br>50<br>100<br>500 | 3.4<br>2.5<br>2.1<br>1.1 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing an epoxide, comprising the step of:
    partially oxidizing an unsaturated hydrocarbon with molecular oxygen in the presence of a reducing substance, with use of a catalyst, said catalyst being arranged so as to include a carrier containing an oxide containing at least one of titanium and zirconium as well as gold fine particles fixed onto said carrier, and to have an acid quantity of not more than 0.1 mmol/g, said acid quantity being derived from a quantity of ammonium that, having been absorbed in said catalyst at temperature of 50° C., is desorbed from said catalyst as the temperature rises from 50° C. to 400° C.

2. The epoxide producing method as set forth in claim 1, wherein said reducing substance is at least one kind of a compound selected from among the group consisting of hydrogen, carbon monoxide, nitrogen monoxide, dinitrogen monoxide, alcohols, aldehydes, phenols, formic acids, oxalic acids, and cyclohexadienes.

* * * * *